(12) United States Patent
Stefanchik

(10) Patent No.: US 6,406,440 B1
(45) Date of Patent: Jun. 18, 2002

(54) SPECIMEN RETRIEVAL BAG

(75) Inventor: David Stefanchik, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/745,664

(22) Filed: Dec. 21, 2000

(51) Int. Cl.[7] .............................................. A61B 10/00
(52) U.S. Cl. ...................................... 600/562; 604/328
(58) Field of Search ................................. 600/562, 543, 600/564; 604/327, 328

(56) References Cited

U.S. PATENT DOCUMENTS

| 5,465,731 A | 11/1995 | Bell et al. ..................... 128/749 |
| 5,465,732 A | 11/1995 | Abele .......................... 128/772 |
| 5,647,372 A | 7/1997 | Tovey et al. ................. 128/749 |
| 5,681,324 A | 10/1997 | Kammerer et al. .......... 606/113 |
| 5,957,884 A | 9/1999 | Hooven ........................ 604/48 |

Primary Examiner—Kevin Shaver
Assistant Examiner—Pamela L Wingood
(74) Attorney, Agent, or Firm—Dean Garner

(57) ABSTRACT

In accordance with the present invention there is provided a surgical instrument for the removal of biological material through an opening within a patient, wherein biological material being larger than the opening within the patient. The surgical instrument includes a specimen retrieval bag having at least one wall. The specimen retrieval bag has an open end, a closed end and a longitudinal axis extending therebetween, wherein the open end is for receiving biological materials therein. The instrument further includes at least one material transfer member attached to the wall adjacent to the open end. The material transfer member extends radially from the wall and is in fluid communication with the bag. Wherein when the open end of the bag is removed from the patient through the opening and the material transfer member is at least partially removed therethrough, a portion of the biological material moves from a portion of the bag within the patient to a portion of the material transfer member outside of the patient to reduce the size of the biological material within the patient.

12 Claims, 7 Drawing Sheets

SPECIMEN RETRIEVAL BAG

FIELD OF THE INVENTION

The present invention relates, in general, to surgical instruments for retrieving tissue and, more particularly, to endoscopic surgical instruments such as pouches or specimen retrieval bags for the removal of tissue through a small incision.

BACKGROUND OF THE INVENTION

Endoscopic surgery is a procedure wherein surgery is performed through a series of small openings or incisions in a patient. This type of surgery reduces or eliminates the need for large incisions and has changed some of the major open surgical procedures such as gall bladder removal to simple outpatient surgery. Consequently, the patient's recovery time has changed from weeks to days. These types of surgeries are used for repairing defects or for the removal of diseased tissue or organs from areas of the body such as the abdominal cavity.

Of interest is the removal or excision of biological material or tissue from the body through a small incision or small natural orifice. Tissue can have many types or forms but fall into three general categories: firm tissue such as muscle and solid tumors, soft tissues such as liver, and fluid filled tissues such as a cyst, a gall bladder, a spleen, or an inflamed appendix. Some tissue can be a mix of multiple categories. For example, an inflamed gall bladder can be a mix of hardened gallstones, fluids such as bile and pus, and an outer covering of firm tissue.

One challenge that exists with minimally invasive surgery is the removal of excised tissue through an opening in the body. A time-honored solution is the manual cutting of the large tissue mass into small pieces that can fit through the incision. However, with this process, fragments of tissue can be dropped and fluids can be spilled into the body cavity. This is serious if the excised tissue is cancerous or infected as this can lead to the seeding and re-spreading of cancer or the spreading of inflammation to healthy tissue.

In answer to the above challenges, surgical pouches or specimen retrieval bags were developed. The specimen retrieval bags are placed endoscopically into an inner cavity of the body, the bags are opened, and the diseased tissue is placed within. The specimen retrieval bags are closed to surround and contain the tissue and fluids within. Thus, the closed specimen retrieval bag prevents the migration of tissue and fluids from the bag into the inner cavity of the body. Once the diseased tissue is placed into the open specimen retrieval bag, the bag is closed and pulled from the inner cavity through an incision or trocar. Drawstrings are typically used to close the specimen retrieval bag in the body and to draw the bag out of the opening in the body. Surgical instruments of this type are described in U.S Pat. No. 5,465,731 by Bell et al. and 5,465,732 by Tovey et al. which are incorporated herein by reference.

Morcellation instruments were also developed that can be used in conjunction with the specimen retrieval bags to chop or dissect large tissue masses within the specimen retrieval bags. When using a morcellation instrument, tissue is placed into the open specimen retrieval bag and the bag opening is partially drawn out of the body, leaving the tissue within the body cavity. Next, the bag is opened and the morcellator is inserted into the bag and into the portion of the bag still within the body cavity to morcellate the tissue. Suction can be used to remove morcellated tissue. A RF morcellation instrument and method of use are described in U.S. Pat. No. 5,957,884 by Michael D. Hooven and a description of morcellation is found in U.S. Pat. No. 5,465,731 by Bell et al. and U.S. Pat. No. 5,465,732 by Tovey et al.

Whereas this method of removing tissue from the body does work, it was awkward for the surgeon to hold the bag open while morcellating and suctioning to remove pieces of tissue. If care is not exercised, the bag can be punctured or the spillage of fluids or and tissue can occur. Additionally, costly, sophisticated specimen retrieval bags are required that are resistant to cutting from the mechanical morcellator blades or RF energy.

U.S. Pat. No. 5,681,324 by Kammerer et al. teaches that a square bottomed pouch (or specimen retrieval bag) enables the tissue specimen to lie across the bottom of the pouch and to impede the removal of the tissue through a trocar site (or incision). More importantly, Kammerer et al. also teaches that a tapered-bottomed pouch solves the square-bottomed pouch problem by aligning the tissue and makes it possible to remove tissue from the body cavity without enlarging the incision. Additionally, the tapered pouch shape reduces the amount of trapped air and reduces the ballooning effect when the pouch is closed and reduces the stress exerted on the pouch and abdominal wall tissue (caused by pulling the pouch through the trocar site or incision). Whereas the tapered pouch did indeed facilitate the removal of tissue, there is room for additional solutions to this problem, particularly when fluids are present within the specimen retrieval bag or within the tissue placed therein.

What is needed is a specimen retrieval bag that offers all of the advantages listed above by providing a pouch or specimen retrieval bag that is easy to remove from the body. Additionally, it would be advantageous to provide an improved specimen retrieval bag that makes it easier for a surgeon to remove a specimen retrieval bag that contains fluids or materials such as chunked or morcellated tissue that that flow under pressure. Presently, there are no known specimen retrieval bags that can provide the surgeon with the improvements and benefits described above.

SUMMARY OF THE INVENTION

In accordance with the present invention there is provided a surgical instrument for the removal of biological material through an opening within a patient, wherein biological material being larger than the opening within the patient. The surgical instrument includes a specimen retrieval bag having at least one wall. The specimen retrieval bag has an open end, a closed end and a longitudinal axis extending therebetween, wherein the open end is for receiving biological materials therein. The instrument further includes at least one material transfer member attached to the wall adjacent to the open end. The material transfer member extends radially from the wall and is in fluid communication with the bag. Wherein when the open end of the bag is removed from the patient through the opening and the material transfer member is at least partially removed therethrough, a portion of the biological material moves from a portion of the bag within the patient to a portion of the material transfer member outside of the patient to reduce the size of the biological material within the patient.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The present invention relates, in general, to surgical instruments for retrieving excised tissue from a patient and, more particularly, to endoscopic surgical instruments such as pouches or specimen retrieval bags for the removal of tissue through a small incision.

The Present Invention Instrument

Figure 1:
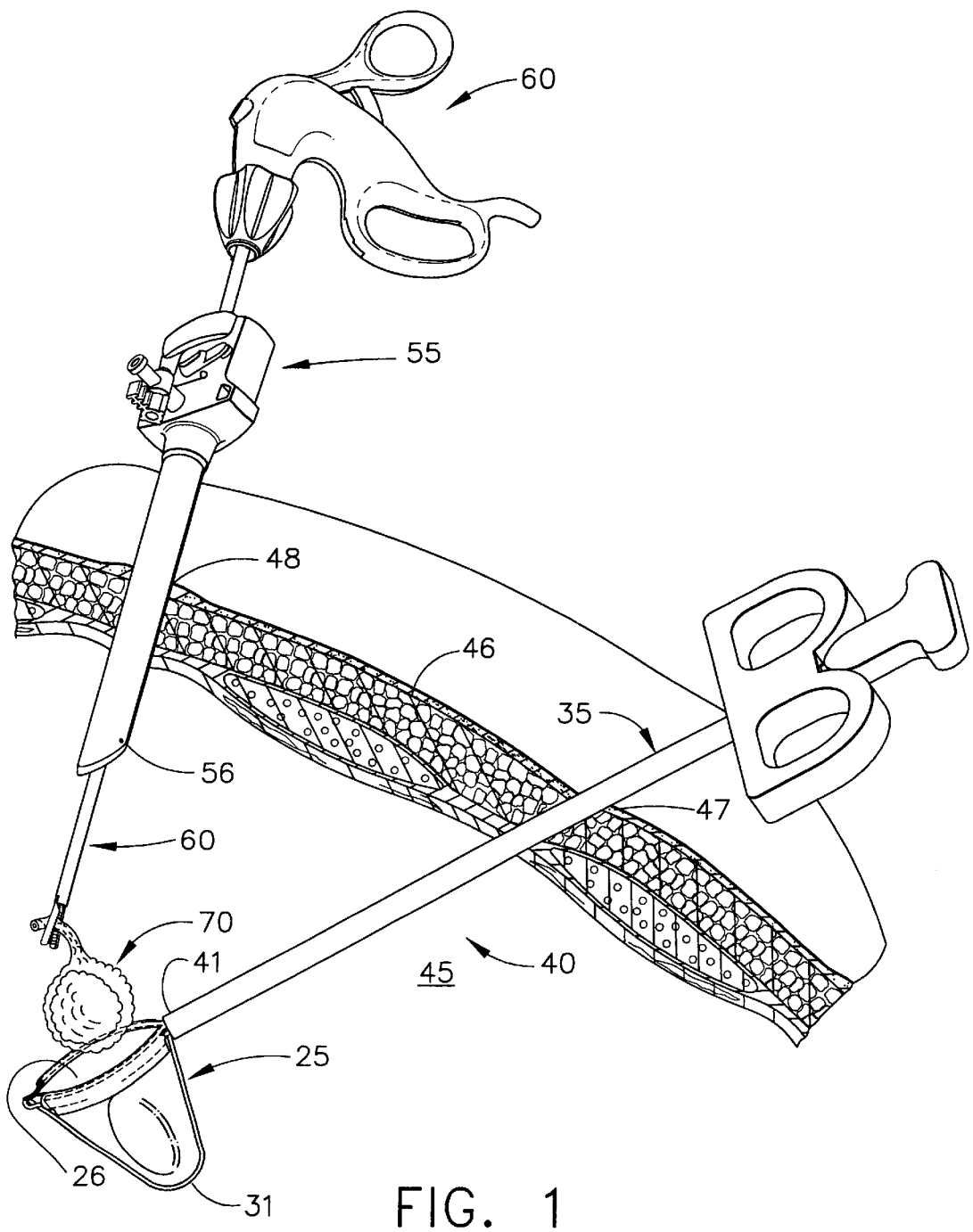
FIG. 1 illustrates an isometric view of a cross section of the abdominal wall and an improved specimen retrieval bag mounted on a specimen retrieval bag instrument, the improved specimen retrieval bag receiving a gall bladder from a surgical grasping instrument within the abdominal cavity.

In FIG. 1, the present invention is an improved specimen retrieval bag 25 shown removably attached to a distal end 41 of a deployment instrument 40. The deployment instrument 40 is shown inserted into an abdominal cavity 45 of a patient through a first incision 47 within a patient's abdominal wall 46. A trocar 55 is inserted into a second incision 48 within the abdominal wall 46 and has a grasping instrument 60 inserted within a cannula 56 (not shown) of the trocar 55. Alternately, if desired, the improved specimen retrieval bag 25 can be drawn into the cannula 56 of the trocar 55 (not shown). Grasping instrument 60 is shown gripping a gall bladder 70 over an opening 26 of the improved specimen retrieval bag 25 just prior to placement of the gall bladder 70 therein.

Figure 2:
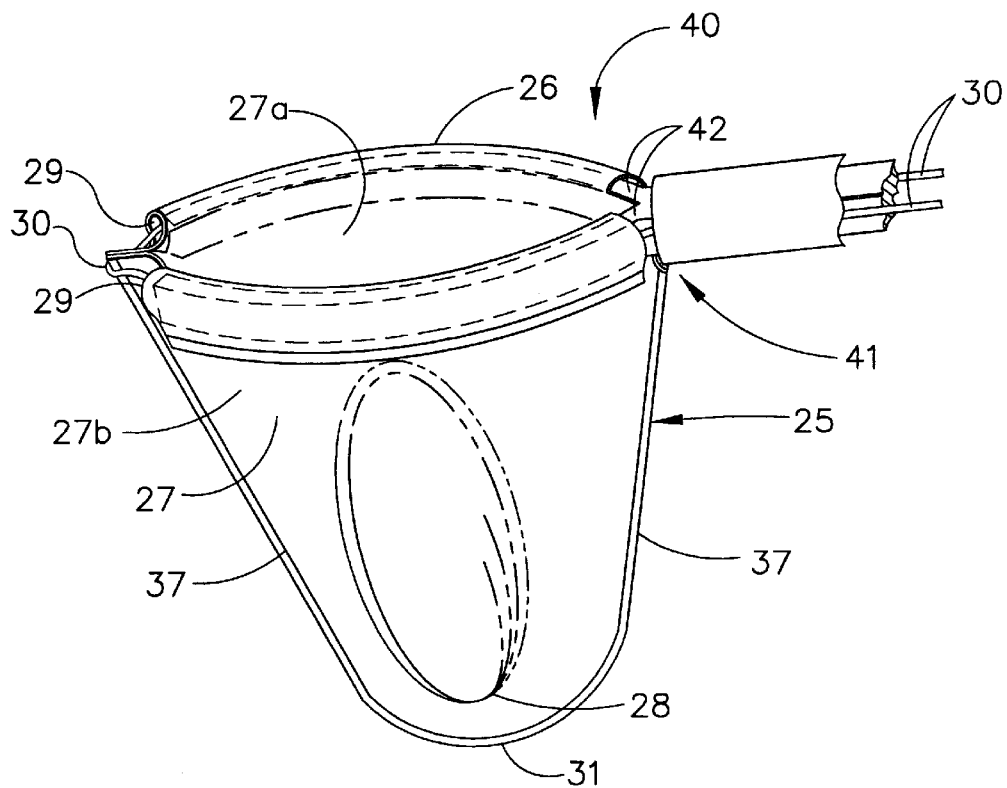
FIG. 2 illustrates an enlarged isometric view of a distal end of the improved specimen retrieval bag instrument of FIG. 1 prior to the receipt of the gall bladder, wherein a novel blister feature extends from a wall of an improved specimen retrieval bag.
Figure 3:
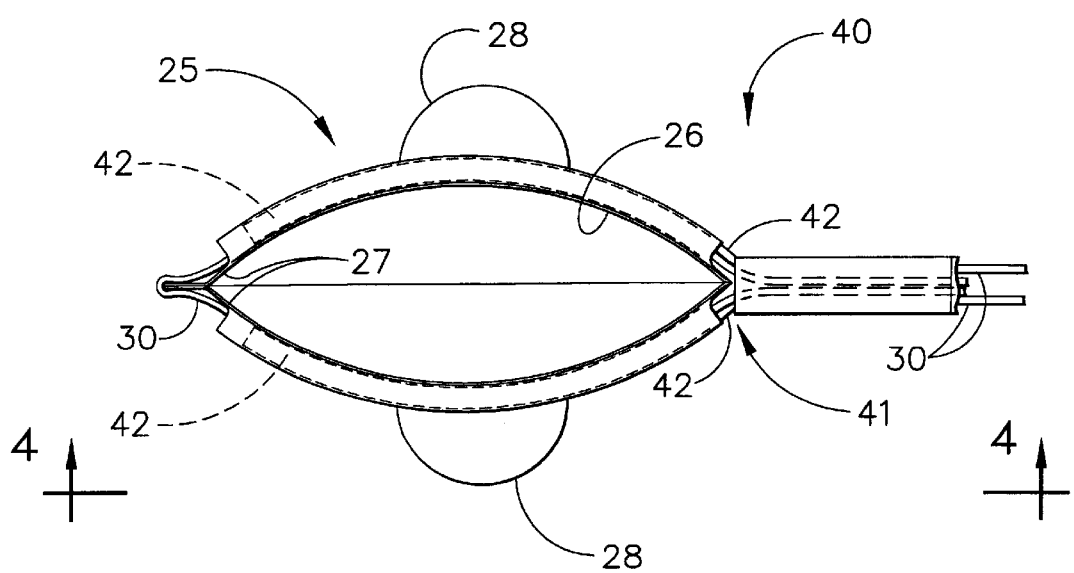
FIG. 3 is a top view of the improved specimen retrieval bag of FIG. 2, wherein the blister features extend outwardly from the walls of the improved specimen retrieval bag.

FIGS. 2 and 3 are enlarged views of the improved specimen retrieval bag 25 of the present invention releasably attached to a distal end 41 of the deployment instrument 40. Improved specimen retrieval bag 25 has two opposing walls 27a and 27b that when joined form a single wall, hereafter referred to as wall 27. The wall 27 is formed from at least one layer of a resilient or flexible material, and has an opening 26 shown in the open position, and a bottom 31. A material transfer member or blister 28 extends outwardly from each wall 27 generally perpendicular to the opening 26 of the improved specimen retrieval bag 25. In FIG. 2 the far side blister 28 is removed for clarity. Channels 29 are located in the improved specimen retrieval bag 25, one along each side of the opening 26. Each channel 29 slidably receives one of a pair of flexible arms 42 extending from the distal end 41 of the deployment instrument 40. When the surgeon desires to detach the improved specimen retrieval bag 25 from the deployment instrument 40, the pair of flexible arms 42 withdraw into the deployment instrument 40 to release the improved specimen retrieval bag 25. A drawstring 30 is threaded through each of the channels 29 and extends into the deployment instrument 40.

Improved specimen retrieval bag 25 of the present invention is formed from a pair of opposed walls 27 that are made of at least one layer of elastomeric or polymeric material. The walls 27 are tapered to facilitate removal of the improved specimen retrieval bag 25 from the first incision 47. Walls 27 are constructed from at least one layer of an elastomeric or polymeric material such as Polyurethane, Polyethylene, Polypropylene, Silicone, Vinyl, or Teflon. Multiple layer construction of the walls 27 are common and can incorporate flexible metal meshes, thermoformed plastic meshes, fabrics, or Kevlar for reinforcement. As shown, walls 27 are formed from flat sheets of Polyurethane and are cut into a desired shape with sides 37 tapered as shown. Blister 28 is formed into a wall 27 by the application of heat, pressure, impact, ultrasonic energy or any combination thereof. Blisters 28 are formed in the wall 27 such that when the walls 27 are loaded in tension such as in the vertical direction at the opening 26 and bottom 31, the stresses travel within in the flat portions of the walls 27 and around the blisters 28. This is somewhat analogous to the manner in which stresses travel around a hole in a part when the part is in tension. The opposed walls 27 are orientated with the blisters 28 extending outwardly as shown, and the walls 27 are sides 37 are glued, heated, or ultrasonically welded together along the sides 37 and bottom 31. Alternately, the Improved specimen retrieval bag 25 can be molded or dip formed into a desired configuration.

Prior Art Instrument Description

Figure 4:
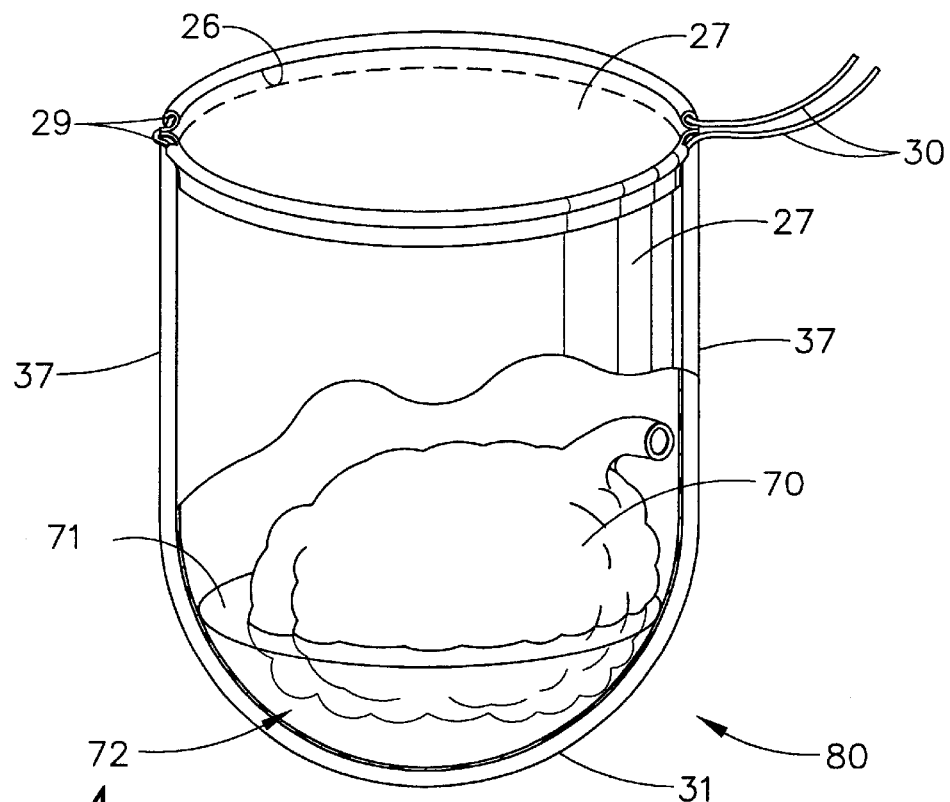
FIG. 4 is an is an enlarged isometric view of a prior art specimen retrieval bag wherein the prior art specimen retrieval bag is open and a gall bladder and fluid are placed therein.

FIG. 4 illustrates a prior art retrieval bag 80. Some of the elements are common to both the prior art bag 80 and the improved specimen retrieval bag 25 bag described previously. When like elements, or nearly identical elements exist, they will have the same element numbers, general descriptions, and generally the same functions. Likewise, generally similar patient anatomy or bag contents will have the same element numbers and descriptions.

As shown in FIG. 4, prior art retrieval bag 80 contains contents 72, an excised gall bladder 70 and fluid 71. The excised gall bladder 70 has been placed into an opening 26 of the prior art retrieval bag 80 and fluid 71 has leaked from the gall bladder 70. Fluid 71 from the gall bladder 70 excision consists of bile, blood, or pus, and any combination thereof. Prior art retrieval bag 80 is attachable (not shown) to the deployment instrument 40 (FIG. 1) in the manner previously described for the improved specimen retrieval bag 25.

Channels 29 are provided surrounding the opening 26 of the prior art retrieval bag 80 for the reception of the flexible arms 42 extending from the deployment instrument 40 (FIG. 1). Drawstring 30 is placed into the channels 29 for closing the opening 26 of prior art retrieval bag 80. Prior art retrieval bag 80 is generally formed from a pair of opposed walls 27 that are made of at least one layer of the materials described above for the improved specimen retrieval bag 25. Sides 37 and bottom 31 are welded, attached or glued together. The sides 37 are not tapered.

Prior Art Instrument—Method of Use and Force Analysis during Removal

Figure 5:
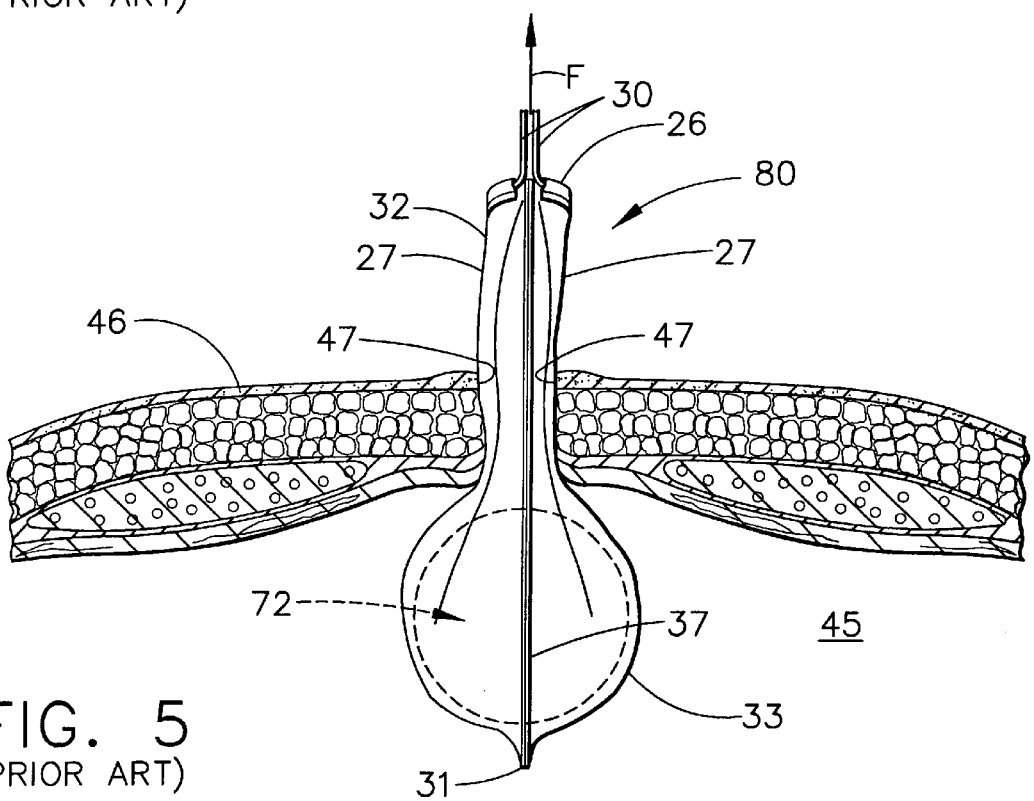
FIG. 5 illustrates a cross-sectional view wherein the opening of the prior art specimen retrieval bag of FIG. 4 is being pulled through an incision within the abdominal wall and the gall bladder and fluid are ballooning the prior art specimen retrieval bag within an abdominal cavity.
Figure 6:
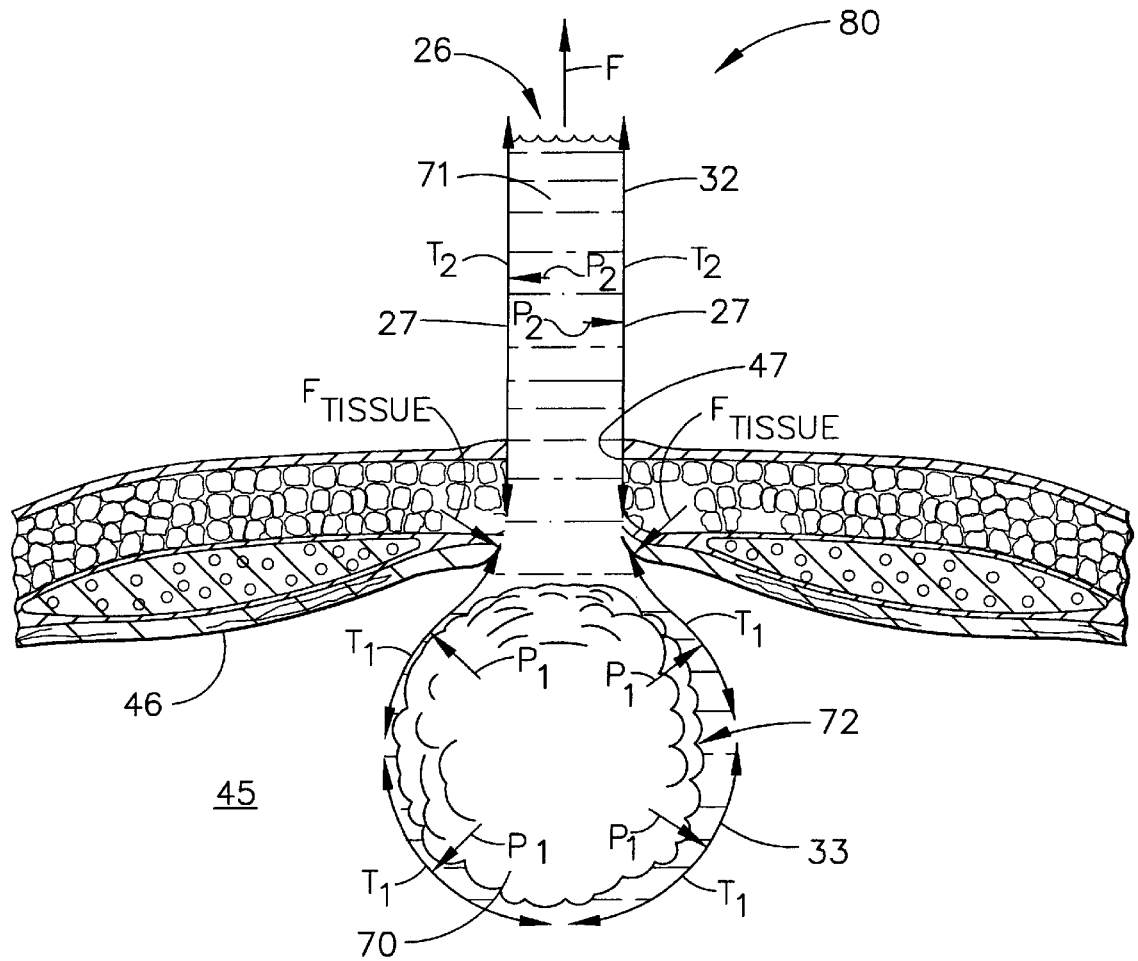
FIG. 6 a cross-sectional view of the abdominal wall and the prior art specimen retrieval bag of FIG. 5, wherein the prior art specimen retrieval bag is being pulled through an incision and the forces exerted upon the prior art bag are shown.

FIGS. 5 and 6 illustrate the method of pulling the prior art retrieval bag 80 containing contents 72 through an incision, and the forces involved in pulling the prior art retrieval bag 80 and the contents 72 through the incision. The description of the method of use of the prior art retrieval bag 80 is provided so that the reader can better understand novel advantages provided with the improved specimen retrieval bag 25 of the present invention which will be discussed in detail below.

As shown in FIGS. 5 and 6, the prior art retrieval bag 80 is being withdrawn from the abdominal cavity 45 of a patient. Prior to the view of FIGS. 5 and 6, the following steps have occurred. First, the prior art retrieval bag 80 has been placed into the patient's abdominal cavity on a deployment instrument 40, and a fluid filled gall bladder 70 is placed therein. The prior art retrieval bag 80 is then closed, released from the deployment instrument 40, and the deployment instrument 40 is then removed from the first incision (not shown).

Next, as shown in FIGS. 5 and 6, an upward tensile force F is applied to the drawstrings 30. This force F is pulling the prior art retrieval bag 80 and contents 72 through the first incision 47 within abdominal wall 46. As shown, the partially removed prior art retrieval bag 80 has an upper columnar shaped portion, henceforth referred to as column 32, which is under tension from force F and extends from the first incision 47. Prior art retrieval bag 80 also has a lower spherical shaped portion referred to as balloon 33 which assumes the spherical shape from the compression of the contents 72 therein. Balloon 33 is located within the abdominal cavity 45 just below the first incision 47.

FIG. 6 is a cross section of the prior art retrieval bag 80 of FIG. 5 showing the balance of physical forces therein as the prior art retrieval bag 80 and contents 72 (gall bladder 70 and fluid 71) are being pulled through the first incision 47. Fluids 71 are present within the contents 72 and are indicated by dashed horizontal lines. The walls 27 of the prior art retrieval bag 80 are replaced with arrows to indicate tensions found within the walls 27 from the forces exerted thereon. The tension arrows will also be referred to as walls 27. As shown in FIG. 6, the upwards motion of the prior art retrieval bag 80 brings the balloon 33 into contact with an inner side of the abdominal wall 46 at first incision 47 and biases the walls 27 of column 32 inwardly. This contact produces a downward and inward abdominal wall contact force $F_{TISSUE}$ on the walls 27 of the balloon. The abdominal wall contact force $F_{TISSUE}$ opposes the tension force F and places the walls 27 of the column 32 under tension as indicated by tension arrows $T_2$.

The upwardly motion of prior art retrieval bag 80 and the inwardly and downwardly abdominal wall contact force $F_{TISSUE}$ squeezes the contents 72 within the balloon 33. As the prior art retrieval bag 80 is pulled through the first incision 47, the balloon 33 gets smaller and the walls 27 of the balloon 33 constrict the contents 72 of the balloon 33 inwardly. The constricting walls 27 of the balloon 33 are opposed by the incompressible contents 72 which exert radially outward pressure vectors $P_1$ on the walls 27 of balloon 33, and the force F creates a tension $T_1$ within the walls 27 of the balloon 33.

The constricting walls 27 force fluids 71 to flow from balloon 33 into the column 32. The opening 26 of the prior art retrieval bag 80 is not fully sealed and air leaks from the opening 26 enabling the fluids 71 to rise within the column 32. The weight of the column of fluids 71 push outwardly with a force $P_{22}$ on the walls 27 of the column 32 and try to bulge the walls 27 above the abdominal wall 46 outwardly. However, the reader is advised to note that the tension forces $T_2$ within the walls 27 of the column 32 are higher than the fluid force $P_{22}$ and the walls remain in the columnar shape of column 32. Thus, tension forces $T_2$ control the volume within the column 32. Fluid 71 can rise into the limited volume defined within the column 32 of the prior art retrieval bag 80 until all of the air flows out of gaps within the opening 26, and the fluid 71 reaches the opening 26. At this point, if the balloon 33 is small enough, the balloon 33 slips through the first incision 47 and the prior art retrieval bag 80 is extracted.

If the balloon 33 is too large to fit through the incision and the column 32 is filled with fluid 71, continuing to draw the prior art retrieval bag 80 out of the first incision 47 can force fluid 71 out of the opening 26 when it is closed. This spillage of fluids 71 complicates the surgery and can require the use of a suction instrument to remove the fluids 71 seeping from the opening 26. In some cases it is necessary to re-open the opening 26 and to use suction or forceps to extract some of the contents 72 therefrom. In some cases, it can be necessary to increase the length of the first incision 47 to remove the prior art retrieval bag 80, or to use scissors or a morcellator on the contents 72 to facilitate removal of the prior art retrieval bag 80.

Improved Instrument—Method of Use and Force Analysis during Removal

Figure 7:
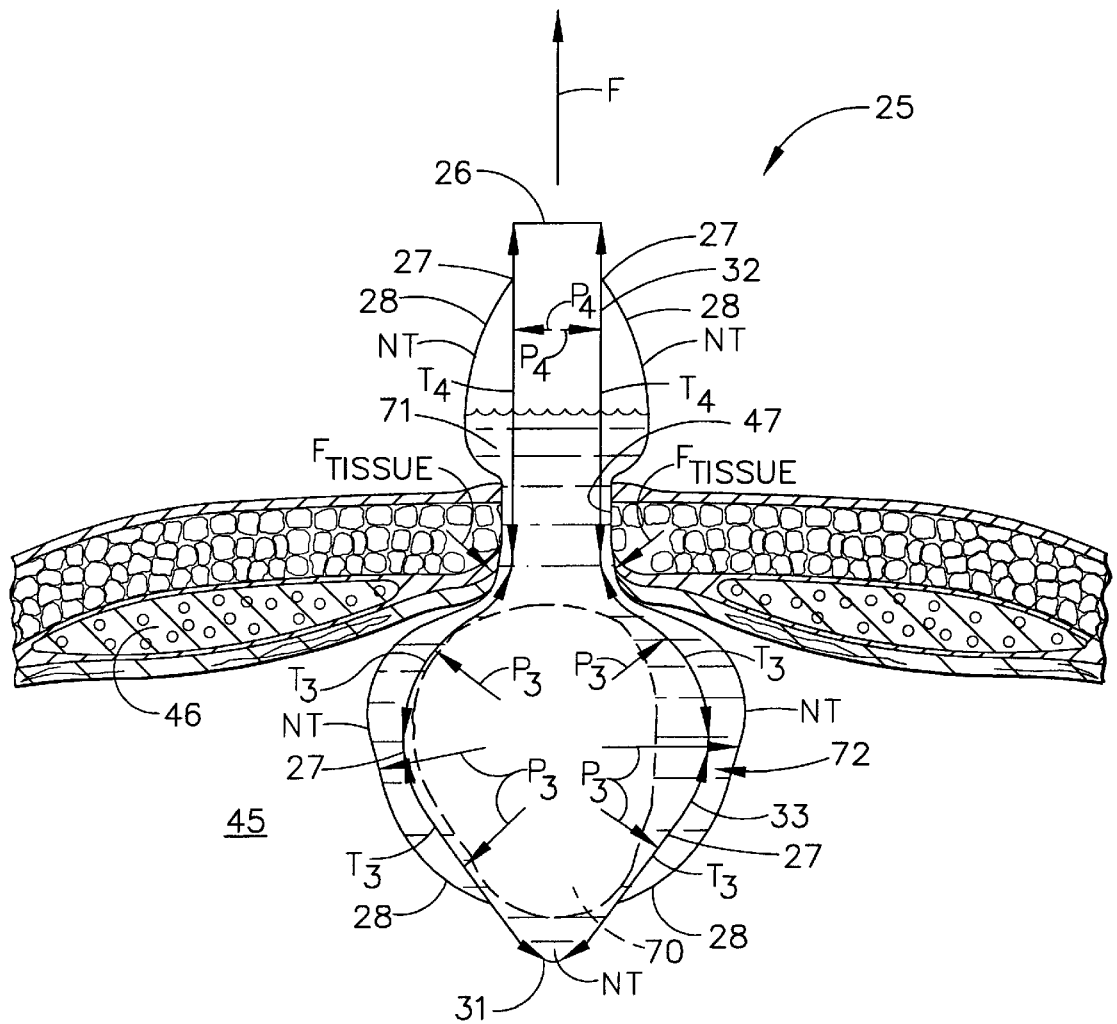
FIG. 7 a cross-sectional view of the abdominal wall and the improved specimen retrieval bag of FIG. 2, wherein the improved specimen retrieval bag is being pulled through an incision with a gall bladder and fluid within, and the forces exerted upon the improved specimen retrieval bag are shown.
Figure 8:
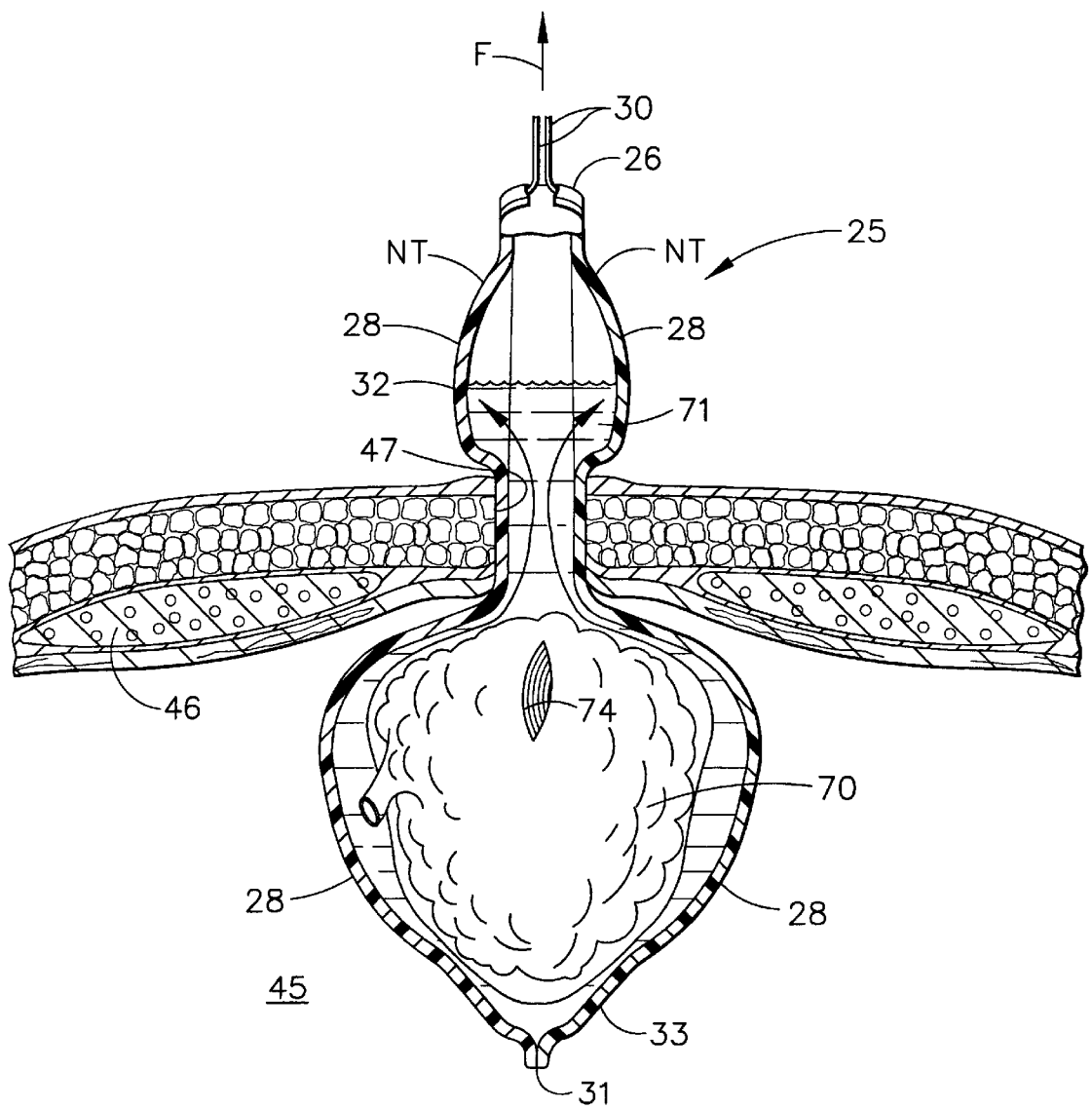
FIG. 8 is a cross sectional view of the of the abdominal wall and the improved specimen retrieval bag of FIG. 7, wherein the improved specimen retrieval bag is being pulled through an incision, and fluids are flowing from a lower portion of the specimen retrieval bag into an upper portion of the blisters of the improved specimen retrieval bag to reduce the size of the lower portion.

FIGS. 7 and 8 are cross-sections of the improved specimen retrieval bag 25 of the present invention being pulled or removed from the first incision 47. These FIGS. illustrate the method of use of the present invention and the balance of forces between the improved specimen retrieval bag 25, the abdominal wall and the contents 72 therein. The reader is advised to review the above sections describing prior art specimen retrieval bag 80 for comparisons.

Prior to the view of FIGS. 7 and 8, the improved specimen retrieval bag 25 on the deployment instrument 40 was placed into the abdominal cavity 45 (FIG. 1) and a gall bladder 70 was placed therein. The improved specimen retrieval bag 25 was closed, and then released from the deployment instrument 40. Finally, the deployment instrument 40 was removed from the first incision 47.

Next, an upward tensile force F is applied to draw the improved specimen retrieval bag 25 and contents 72 consisting of gall bladder 70 and fluid 71 through the first incision 47 and out of the patient. FIG. 7 shows a cross section of the improved specimen retrieval bag 25 (taken across the blisters 28) as it is being partially drawn upwards through the first incision 47 by tensile force F.

The cross section of FIG. 7 is taken across the blisters 28 of the improved specimen retrieval bag 25 and shows the forces involved therein. As described previously, the walls 27 and the blisters 28 are designed such that when the walls 27 are placed under tension (from the force F), the tensile forces travel within the walls 27 and around the blisters 28. Thus, the upper force F exerts tension on the walls 27 and not on the blisters 28. In FIG. 7 walls 27 are outlined by the tension arrows $T_3$ and $T_4$. The blisters 28 are not under tension from the force F.

The contents 72 of the improved specimen retrieval bag 25 are being compressed or constricted within the balloon 33 and exert an outwards force $P_3$ on the portion of the walls 27 and blister 28 of the balloon 33. In FIG. 7, the contents 72 consist of gall bladder 70 and fluid 71. The upwards motion of the improved specimen retrieval bag 25 constricts the contents 70 of the balloon 33 and forces the fluid 71 to rise into the portion of the improved specimen retrieval bag 25 extending above the incision 47. The constriction compresses the contents 72 within the balloon 33 and the contents 72 exert a radially outwards force $P_3$ on the portion of the walls 27 and blister 28 of the balloon 33. This outward pressure has tensioned the walls 27 of the balloon 33 as indicated by the tension arrows $T_3$, and has expanded blisters 28 outwardly from the balloon 33.

As the improved specimen retrieval bag 25 is advanced upwardly by force F, fluid 71 moves upwardly from the constricted balloon 33 and into the column 32, expanding the non-tensioned portions NT of the blisters 28 outwardly outside of the incision 47. This movement of fluids 71 into the non-tensioned portions NT of the blisters 38 reduces the size of the contents of the balloon 33, enabling the improved specimen retrieval bag 25 to be pulled farther out of the first incision 47. As more of the improved specimen retrieval bag 25 moves out of the body, more the non-tensioned portions NT of the blisters 38 emerge from the first incision 47 and more fluids 71 can move upwardly from the balloon 33 into the non-tensioned portions NT of the blisters 28. This fluid transfer process continues until the improved specimen retrieval bag 25 and contents 72 are easily extracted from the patient.

FIG. 8 is a cross-section of the improved specimen retrieval bag 25 across vertical axis B—B and the blisters 28 showing an embodiment of the method steps of using the present invention to remove a fluid filled organ such as a gall bladder 70. Gall bladder 70 is first placed into the improved specimen retrieval bag 25 and a cut 74 is placed into the gall bladder 70 to release the fluids 71 within. Next, the improved specimen retrieval bag 25 is closed, and the improved specimen retrieval bag 25 is pulled out of the first incision 47. As shown, pulling the improved specimen retrieval bag 25 through the first incision 47 compresses the gall bladder 70, squeezing fluids 71 from the cut 74. The flow of fluids 71 from the gall bladder 70 reduces the size of the organ and makes it easier to draw the organ through the first incision 47. As described above, the fluids 71 flow easily from the cut 74 within the squeezed gall bladder 70, into the column 32 and into the non-tensioned portions NT of the blisters 28. This flow of fluids 71 into the non-tensioned portions NT of the blisters 28 reduces the size of the balloon 33, and facilitates the removal of the improved specimen retrieval bag 25 from the patient.

Figure 9:
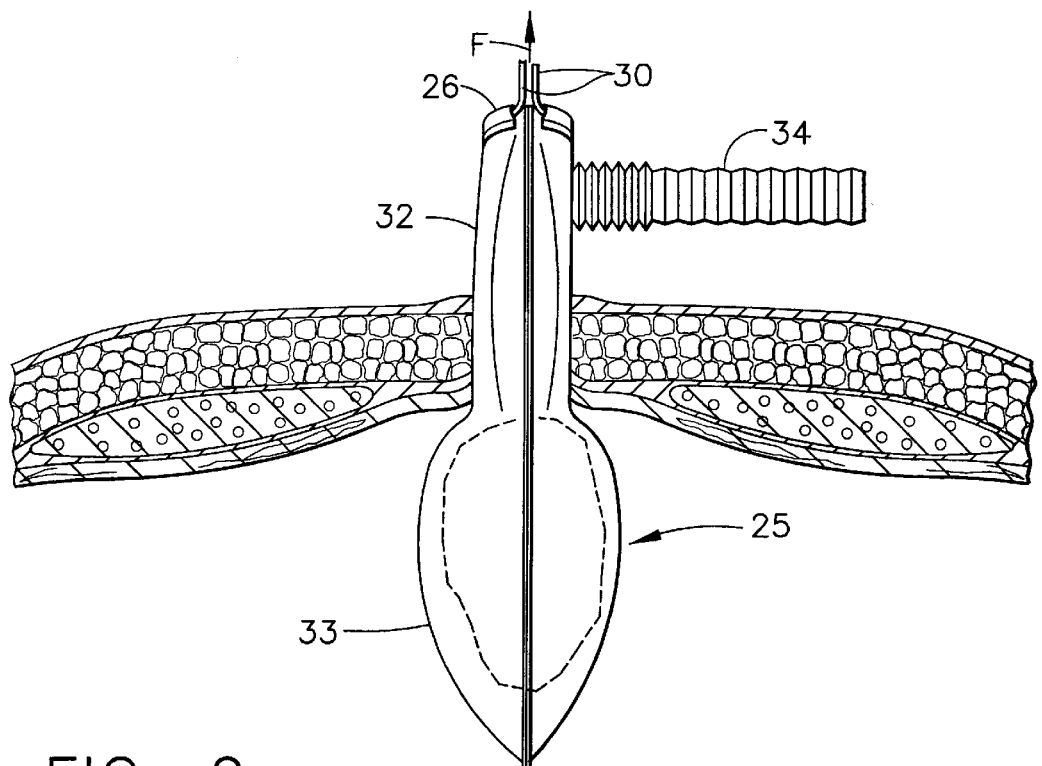
FIG. 9 is a cross sectional view of the of the abdominal wall wherein a first alternate embodiment of the improved specimen retrieval bag of FIG. 5 is shown.
Figure 10:
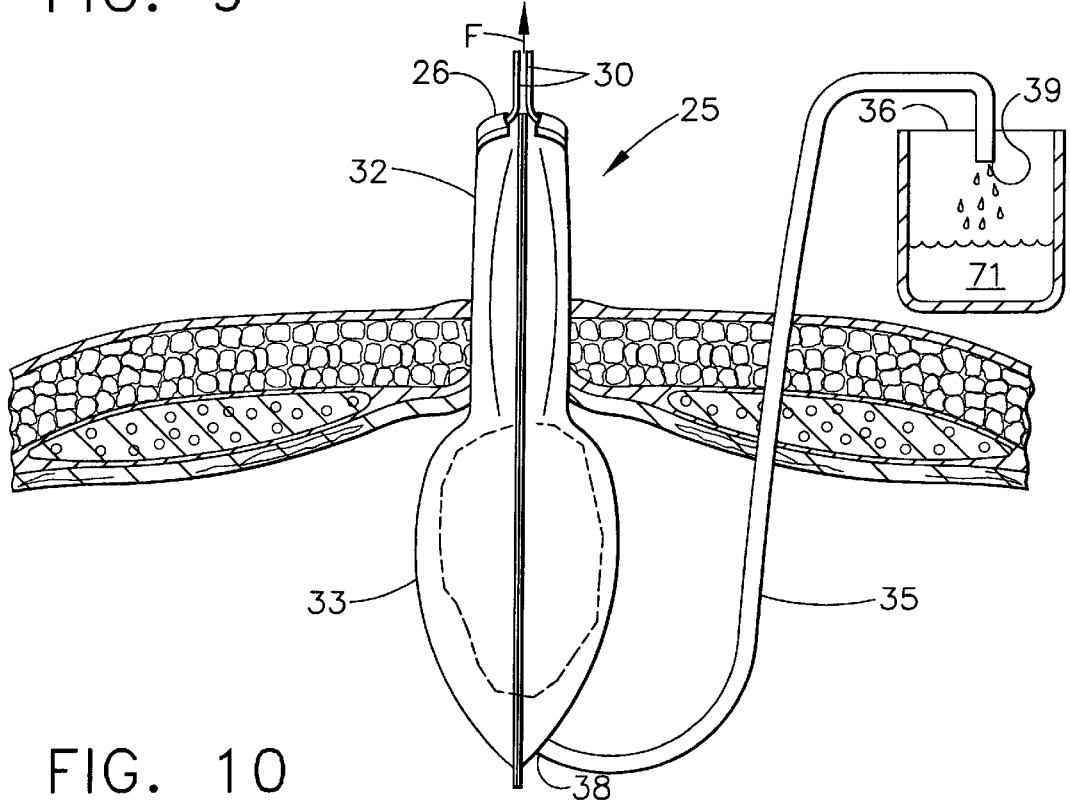
FIG. 10 is a cross sectional view of the of the abdominal wall wherein a second alternate embodiment of the improved specimen retrieval bag of FIG. 5 is shown.

FIGS. 9 and 10 illustrate alternate embodiments of the improved specimen retrieval bag 25. FIG. 9 shows an alternate embodiment of improved specimen retrieval bag 25 bag without blisters 28 but having an expandable element located adjacent to the opening 26. As shown, the expandable element is a bellows 34 that easily expands outwardly when pressurized. As the bellows 34 expands outwardly, fluids flow from the balloon 33, into the column 32 and into the bellows 34. Alternately, placing an elastomeric panel placed within the walls 27 of the improved specimen retrieval bag 25 will also meet the intent of the alternate embodiment.

FIG. 10 shows yet another alternate embodiment of the improved specimen retrieval bag 25 having an alternate embodiment of the transfer portion for the transport of fluids out of the patient. This alternate transfer portion has a hollow fluid passage 35 for the transfer of fluid from the balloon 33 into a receptacle 36 located outside of the abdominal wall 46. Hollow fluid passage 35 has a first end and a second end. Pulling the balloon 33 through the first incision 47 moves fluids 71 through the hollow fluid passage 35 and into the receptacle 36.

Whereas the above descriptions describe a fluid 71 as a substance such as blood, bile, pus, or other bodily liquid, it is conceivable that other materials may be considered as liquids or fluids in certain situations. For example, morcellated tissue is of a paste-like consistency and can be made to flow (like a fluid) within a confined container with pressure. Additionally, pieces of other solid or semisolid materials (such as tissue or dry substances) can be made to move in a more fluid-like manner when combined with a fluid 71, which acts as a lubricant. Thus, the addition of a fluid 71 such as saline, water, (or any one of a number of other liquids) to the improved specimen retrieval bag 25 can aid in the movement of tissue within the bag. Thus the fluids 71 described above can encompass a much wider range of materials than those listed above, including morcellated tissue, and in some cases, larger pieces of tissue.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical instrument for the removal of biological material through an opening within a patient, the biological material being larger than the opening within the patient, the surgical instrument comprising:

a. a specimen retrieval bag having at least one wall, said specimen retrieval bag having an open end, a closed end and a longitudinal axis extending therebetween, said open end for receiving biological materials therein; and b. at least one material transfer member attached to said wall adjacent to said open end, said material transfer member extending radially from said wall and being in fluid communication with said bag, wherein when said open end of said bag is removed from the patient through the opening and said material transfer member is at least partially removed therethrough, a portion of the biological material moves from a portion of said bag within the patient to a portion of said material transfer member outside of said patient to reduce the size of the biological material within the patient.

2. The surgical instrument of claim 1 wherein said material transfer member is at least one expandable element near to said open end.

3. The surgical instrument of claim 2 wherein said at least one expandable element is a bellows.

4. The surgical instrument of claim 1 wherein said wall is fabricated from a polymeric material.

5. The surgical instrument of claim 4 wherein said polymeric material is Polyurethane.

6. The surgical instrument of claim 1 wherein said specimen retrieval bag is tapered, said specimen retrieval bag larger at said open end and smaller at said closed end.

7. The surgical instrument of claim 1 wherein said specimen retrieval bag has a drawstring for closing the open end of the specimen retrieval bag.

8. A surgical instrument for the removal of biological material through an opening within a patient, the biological material being larger than the opening within the patient, the surgical instrument comprising:
   a. a specimen retrieval bag having at least one wall, said specimen retrieval bag having an open end and a closed end, said open end for receiving biological materials therein; and
   b. at least one outwardly disposed blister on said wall, wherein when said specimen retrieval bag and said blister are partially removed from the patient through the opening, a portion of the biological material moves within said blister moving said material from a portion of said bag within the patient to a portion of said bag outside of said patient to reduce the size of the biological material within the patient.

9. The surgical instrument of claim 8 wherein said wall is fabricated from a polymeric material.

10. The surgical instrument of claim 9 wherein said polymeric material is Polyurethane.

11. The surgical instrument of claim 8 wherein said specimen retrieval bag is tapered, said specimen retrieval bag larger at said open end and smaller at said closed end.

12. The surgical instrument of claim 8 wherein said specimen retrieval bag has a drawstring for closing the open end of the specimen retrieval bag.

* * * * *